United States Patent [19]

Csatary et al.

[11] Patent Number: 5,124,148

[45] Date of Patent: Jun. 23, 1992

[54] METHOD FOR TREATING VIRAL DISEASES WITH ATTENUATED VIRUS

[75] Inventors: Laszlo K. Csatary, Ft. Lauderdale, Fla.; Richard J. Massey, Rockville, Md.

[73] Assignee: United Cancer Research Institute, Alexandria, Va.

[21] Appl. No.: 744,438

[22] Filed: Aug. 13, 1991

Related U.S. Application Data

[63] Continuation-in-part of Ser. No. 186,940, Apr. 27, 1988, abandoned.

[51] Int. Cl.$^5$ .................. A61K 39/12; A61K 39/42
[52] U.S. Cl. ................................. 424/86; 424/88; 424/89
[58] Field of Search ........................ 424/86, 88, 89

[56] References Cited

U.S. PATENT DOCUMENTS

| | | | |
|---|---|---|---|
| 3,548,054 | 12/1970 | Bowen | 424/89 |
| 3,577,525 | 5/1971 | Baker | 424/89 |
| 4,053,582 | 10/1977 | Stickl | 424/89 |
| 4,108,983 | 8/1978 | Wallack | 435/235.1 |

FOREIGN PATENT DOCUMENTS

1274820  5/1972  United Kingdom .

OTHER PUBLICATIONS

Csatary et al., "Interference Between Human Hepatitis A Virus and An Attenuated Apathogenic Avian Virus", Acta Microbiologica Hungarica 31(2)153–58 (1984).

Primary Examiner—Nathan M. Nutter
Attorney, Agent, or Firm—Sixbey, Friedman, Leedom & Ferguson

[57] ABSTRACT

A method for treating human disease of viral etiology which employs the administration of a pharmaceutically effective amount of a live attenuated virus. Avian paramyxovirus is the virus preferred for use in live attenuated vaccine form, although other viruses of human and nonhuman origin have also been shown to be effective. The administration of a pharmaceutically effective amount of avian paramyxovirus and avian rotavirus vacciine has been shown to be efficacious in the treatment of Herpes virus infections, hepatitis-A, some cancers, aphthous stomatitis, acquired immune deficiency syndrome (AIDS) and polyarteritis nodosa.

9 Claims, 1 Drawing Sheet

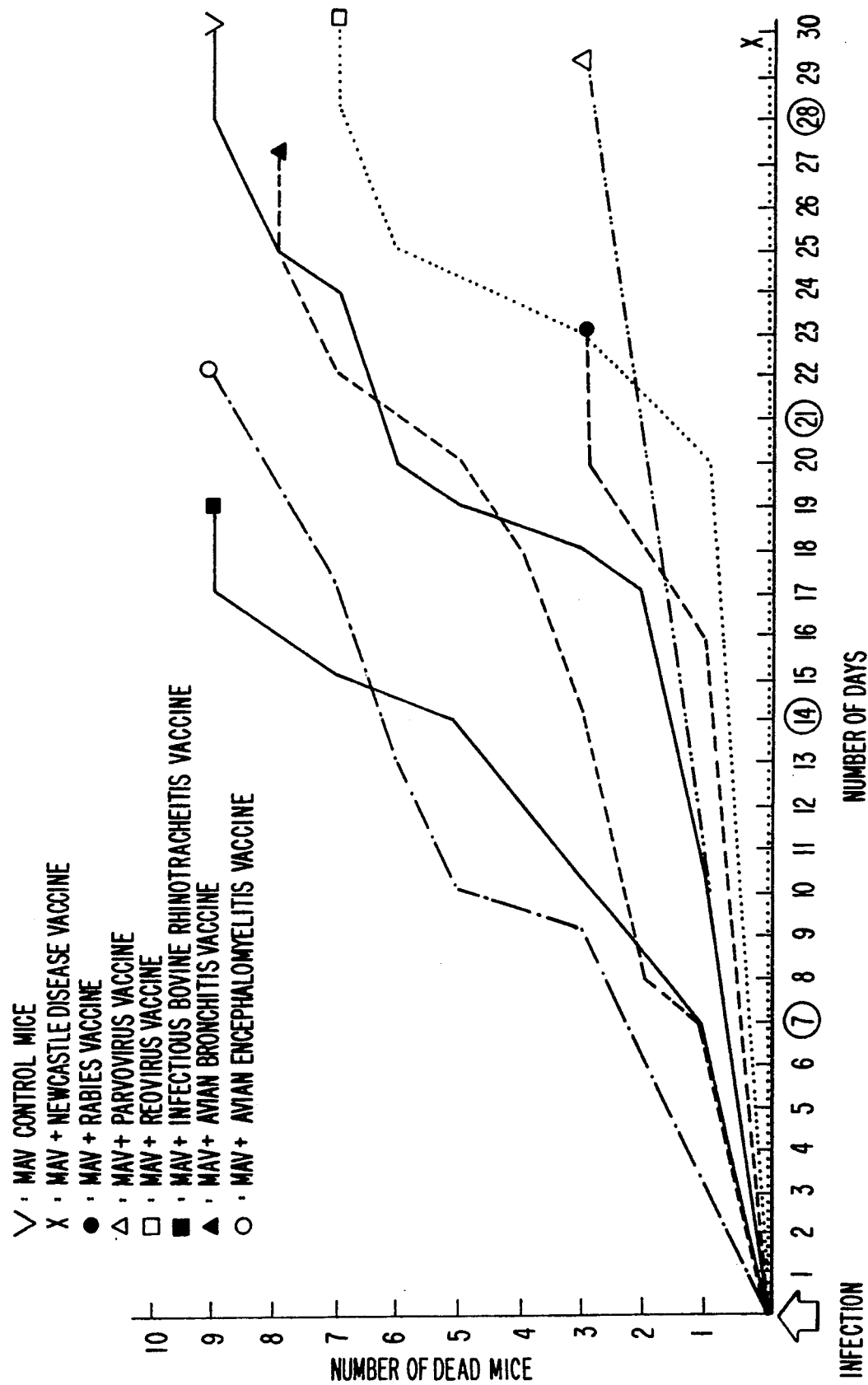

METHOD FOR TREATING VIRAL DISEASES WITH ATTENUATED VIRUS

This is a continuation-in-part of United States Patent Application Ser. No. 07,186,940, filed Apr. 27, 1988 and now abandoned.

TECHNICAL FIELD

The present invention relates generally to a method for treating and/or controlling diseases of viral origin and, more particularly, to a method for treating human diseases of viral etiology which employs the administration of a pharmaceutically effective amount of an attenuated virus.

BACKGROUND ART

Until recently, human diseases of viral etiology have proved to be very difficult, if not impossible, to treat successfully. Chemical antiviral agents currently comprise the most widely used treatment. Some chemical antiviral agents, however, such as, for example, azidothymidine (AZT), may cause serious and unpleasant side effects which lead to the contraindication of their use in many patients infected with viral diseases. In addition, the high cost typically associated with many of these chemical agents may effectively preclude access to such treatment by many in need. In addition, the chemical antiviral agents are generally not equally effective against a broad spectrum of viruses. Such antiviral agents, therefore, have a more limited usefulness for the general population than may be desired Consequently, researchers have turned their attention to the development of other methods of achieving antiviral activity to combat diseases of viral etiology that have proved refractory to available therapies.

As the mechanisms of viral infection have become better understood, approaches to combating human diseases of viral etiology based on these mechanisms have began proposed. For example, Baker in U.S. Pat. No. 3,577,525 suggests a method of inducing resistance to infectious viruses in animals. An essential aspect of Baker's method employs a virus or bacterium alien to the animal to develop complement-fixing antibodies in the animal to the infectious virus. In addition, the alien virus or bacterium must be immunologically unrelated to the infectious virus. Baker's method is disclosed to be an effective method of protecting a horse against infectious equine rhinopneumonitis by the use of bovine rhinotracheitis virus to produce in the horse complement-fixing antibodies against the equine rhinopneumonitis virus. Although this method may effectively induce immunity to viral infections in animals, there is no suggestion that it has any application to the treatment of viral diseases in humans already infected with /the virus.

U.S. Pat. No. 4,053,582 to Stickl suggests the attenuation of fowl pox virus to form a new virus no longer pathogenic to fowl which induces the production of interferon. This new virus is suggested to be capable of administration to animals and humans to treat a wide variety of infectious diseases. The level of interferon production achieved by this new virus in animals appears to depend on the route by which the virus is administered. Although this patent suggests the rather widespread application of the attenuated fowl pox virus to infectious disease of both viral and bacterial etiology, the only specific examples presented relate to the treatment of herpes, influenza and viral warts in humans and to the treatment of certain virus-caused animal infections, such as equine influenza and pigsty epidemic. Although the new viral strain disclosed in this patent may treat these conditions effectively, there is no suggestion that its efficacy extends further to encompass other human diseases of viral etiology, such as hepatitis, viral neoplastic disease or acquired immune deficiency syndrome.

Cancer research has for years focused on identifying causative viral agents in the hopes that vaccines specific to these causative agents could be developed. While the successful identification of such specific causative agents has thus far not been fully achieved, researchers have suggested the use of antitumor viral agents to treat various mammalian tumors. For example, Wallack, in U.S. Pat. No. 4,108,983, discloses using the vaccinia virus (the agent used to make currently available smallpox vaccines) to lyse species-specific tumor cells and produce an injectable oncolysate that appears effective in treating some kinds of tumors. However, the production of this antitumor agent is dependent upon obtaining a sample of tumor cells from the specific patient to be treated, either surgically or otherwise, to produce the antitumor oncolysate. Consequently, this method is not likely to have widespread efficacy.

Japanese Publication No. 58-116422 discloses an antitumor agent that contains a live vaccine of attenuated paramyxovirus which exhibits an antitumor effect in mice. The antitumor agent described in this publication is not disclosed to be effective against conditions other than the specific mouse tumors studied.

An additional infectious disease of viral etiology that has increasingly become the focus of public attention in recent years is human acquired immune deficiency syndrome (AIDS). Although chemical antiviral agents such as AZT have been used to treat AIDS with some success, these agents suffer from disadvantages, such as the side effects previously mentioned, as well as their high cost. While much research effort has been directed to identifying treatments effective against AIDS, this effort has focused primarily on the development of potential chemical pharmacological and pharmaceutical agents. It has not been suggested to employ a virus in the treatment of AIDS.

The prior art, therefore, fails to suggest a method for treating human diseases of viral etiology which employs an antiviral agent that is readily available and easily produced and which employs as the specific antiviral agent an attenuated virus and which is effective in treating a wide spectrum of diseases of viral etiology, many of which pose major public health problems.

SUMMARY OF THE INVENTION

It is, therefore, a primary object of the present invention to overcome the disadvantages of the prior art and to provide a method for treating a broad spectrum of human diseases of viral etiology.

It is yet another object of the present invention to provide a method for treating a broad spectrum of human diseases of viral etiology which employs the administration of a pharmaceutically effective amount of an attenuated virus.

It is still another object to provide a method for treating a broad spectrum of human diseases of viral etiology which comprises the administration of an attenuated virus selected from the group consisting of avian paramyxovirus and avian rotavirus.

It is yet another object to provide a method for treating infections caused by viruses of the Herpes group.

It is yet a further object to provide a method for treating viral neoplastic diseases.

It is still a further object to provide a method for treating infections caused by hepatitis viruses It is an additional object to provide a method for treating aphthous stomatitis.

It is yet an additional object to provide a method for treating human acquired immune deficiency syndrome (AIDS).

The aforesaid objects are achieved by providing a method for treating human diseases of viral etiology which includes the administration of a pharmaceutically effective amount of a preparation containing an attenuated virus. A broad spectrum of human viral diseases as well as some diseases of unknown etiology, has been found to be treated effectively by the administration of a pharmaceutically effective amount of an attenuated virus, particularly certain types of avian paramyxovirus and rotavirus. Successful treatment of infections caused by Herpes viruses, hepatitis viruses and human immunodeficiency virus as well as certain kinds of cancers, primarily adenocarcinomas, has been achieved by this method. In addition, successful treatment of diseases of unknown etiology, such as aphthous stomatitis and arthritis, has also been achieved. Other viruses, such as human paramyxovirus, rotavirus and also adenovirus may be employed in accordance with the present method to treat human diseases of viral and unknown etiology.

Other objects and advantages of the present invention will be apparent to those skilled in the art from the following detailed description, examples and claims.

BRIEF DESCRIPTION OF THE DRAWINGS

The sole drawing illustrates in graphic form the interference between Mouse Ascites Associated Lymphoma Virus (MAV) and seven selected animal viral vaccines.

BEST MODE FOR CARRYING OUT THE INVENTION

The phenomenon known as viral interference, wherein a noninfective virus interacts with an infective virus to "interfere" with the infective virus and render it noninfective or avirulent, has been known for some time. However, the importance of this phenomenon in treating diseases of viral etiology has only recently been considered. The potential application of this phenomenon in the treatment of certain human viral diseases was not even recognized until the present invention. In the past, efforts to apply the phenomenon of viral interference to the treatment of human diseases of viral etiology have focused primarily on the identification and isolation of interfering substances produced by the noninfective virus. The interferons are the main interfering substances that have been identified, isolated and administered in the treatment of human viral diseases. However, their success has been limited.

The present method of treating viral diseases was developed following observations that persons suffering from diseases of viral etiology who were subsequently exposed to the viral infections of other species caused by viruses apathogenic to humans experienced significant improvement and, in some cases, an apparent cure of the disease. These observations ultimately led to the present invention. These initial observations, which documented the exposure of the infected person to a viral disease that infects only chickens, known as avian paramyxovirus or Newcastle disease, formed the basis for the research leading to the present invention. Not only were studies directed to the avian paramyxovirus, but also to other viruses in attenuated form apathogenic to humans which appear to be capable of achieving similar results.

Because of the commercial importance to the poultry industry of the treatment and control of Newcastle disease, much effort has been expended in developing an effective vaccine to be used to immunize poultry against the avian paramyxovirus which causes this disease. As a result, available paramyxovirus vaccines have been highly refined and are quite effective against the avian paramyxovirus. Illustrative of the available avian paramyxovirus vaccines is the attenuated live vaccine described in British Patent No. 1,274,820.

Several strains of avian paramyxovirus vaccine have been developed and are described by Hanson and Brandley in "Identification of Vaccine Strains of Newcastle Disease Virus," Science, 112, 156–157 (1955). The $B_1$ strain, which is of chick embryo origin, is too weak to induce the signs of Newcastle disease or avian paramyxovirus in chickens, but will produce antibodies effective against the more virulent forms of the virus. A method of producing the $B_1$ strain of Newcastle disease virus vaccine,,is described by Bowen et al in U.S. Pat. No. 3,548,054. The $B_1$ strain of Newcastle disease virus vaccine is available in freeze dried form and typically contains 1000 chicken doses or units per vial. One commercial source of avian paramyxovirus vaccine, $B_1$ Type, $B_1$ Strain, is Salsbury Laboratories, Charles City, Iowa. This vaccine can be used effectively in the treatment method described herein.

The avian paramyxovirus preparation preferred for use in the present treatment method is a highly purified, intact attenuated virus preparation. The preferred method of attenuation is based on the sequential propagation of the virulent virus to produce an attenuated form. Although the attenuated form of virus is the preferred treatment agent, other viral forms, namely the inactivated virus and viral components, such as purified RNA, could also be used and are additionally contemplated to be within the scope of the present invention. A preferred avian paramyxovirus vaccine is derived from avian paramyxovirus vaccine strain H. It has been shown to be safe for use in humans, and no complications or side effects have been demonstrated or reported, although it has not been given to pregnant women. The pharyngitis, coryza and bronchitis which usually accompany the administration of a preparation that includes the intact virion of an attenuated virus have been notably absent following the administration of avian paramyxovirus vaccine.

The preferred avian paramyxovirus vaccine used in the examples discussed below is clear and colorless to slightly yellowish and is manufactured in an aqueous suspension without added preservatives. It is preferably lyophilized or kept frozen until use and is readily soluble in normal saline solution. Each milliliter is equivalent to one thousand (1,000) reference units. Avian paramyxovirus has been determined to cross the blood-brain barrier, and the degree of CNS penetration is still under investigation. Toxicity studies including clinical trials involving 5 patients, however, have demonstrated that Strain H attenuated avian paramyxovirus vaccine is nontoxic.

Although the specific dosage of the avian paramyxovirus vaccine administered will vary and is dependent on many factors, such as the particular viral disease being treated, the route of administration, the age and condition of the patient, and the concurrent administration of other pharmaceuticals that may have a potentiating effect, a pharmaceutically effective amount of Strain H or Strain $B_1$ avian paramyxovirus vaccine may range from about 1000 units per week to 4000 or more units per day (e.g., 1000 units 4 times daily) for at least a 30-day period followed by 4000 units every two days when the vaccine is administered by intramuscular injection. Intravenous administration of the vaccine will lower the dose to about 250 units rather than 1000 units. 1000 reference units of avian paramyxovirus is equivalent to 1000 chicken doses of strain $B_1$ vaccine.

Avian paramyxovirus vaccine may be administered through any of the usual routes for administering medication: intravenous, intramuscular, intrastomal, oral, rectal, intranasal and topical. Avian paramyxovirus vaccine is readily absorbed through the mucous membranes. Intranasal administration has been shown to be particularly effective in many cases. However, in some instances parenteral administration may be more effective. The vaccine is usually supplied in lyophilized or freeze-dried form. Therefore, the recommended dose, which as noted above depends on many factors, can be diluted in 1.5 ml normal saline for intramuscular injection, or it may be administered in 500 ml 5% dextrose in water or normal saline over 1 hour. The dry, lyophilized powder may also be administered without the addition of liquid, for example directly to herpes lesions.

In addition to employing the avian paramyxovirus in attenuated form, both the inactivated and purified forms have proven to provide treatment equally effective as the attenuated virus.

While avian paramyxovirus has been the virus tested the most extensively in the present treatment method, some testing of the use of other viruses has also been conducted. These viruses have been in the form of attenuated virus vaccines. The primary utility of some of these attenuated viruses up until now has been as veterinary vaccines, since the viruses in question are pathogenic to animal species other than humans. These viruses include avian rotavirus, avian herpes virus, avian bronchitis virus and avian encephalitis virus. None of these viruses, even though quite pathogenic and virulent in chickens, is known to be pathogenic to humans The foregoing viruses were administered in live attenuated form, such as the form used in the preparation of prophylactic vaccines, in the present treatment method.

Of the aforementioned viruses the avian rotavirus, used in the attenuated form propagated in primary or secondary fibroblast cultures from 10 to 11 day chick embryos has been tested most extensively. The avian rotavirus vaccine used in the treatment method described herein should preferably be made from sterile virus material of at least $10^6$ $TCLD_{50}/0.1$ ml and 50% skim milk, which is then freeze-dried and stored in 2.0 ml amounts. This avian rotavirus vaccine was tested for safety in 3 week old specific pathogen free (SPF) chickens and has not exhibited toxicity to humans. The dose of avian rotavirus vaccine used depends on the patient treated, the actual composition of the preparation, the state of the disease and the particular virus strain used. When the attenuated avian rotavirus is administered, a daily single dose of 1000 to 5000 units and preferably 3000 to 4000 units should be given. This dosage may also be divided into 2 to 5 doses. The administration of this amount for six consecutive days generally is sufficient to produce the desired treatment effect. Administration of the attenuated virus can be by any of the customary routes: intravenous, intramuscular, oral, rectal, intranasal, intrastomal and topical, in the form of a solution or ointment.

It has been discovered that the addition of a potentiating agent to the attenuated avian rotavirus will potentiate the action of the virus While chlorpromazine has thus far proved to be the most effective and, therefore, is preferred for use as a potentiating agent, other potentiating agents may also be employed. Possible potentiating agents also include promethazine, methophenazine, aminopromazine and the like. The potentiating agent is preferably used at a daily dose level of 10 to 100 mg for each 1000 units of attenuated avian rotavirus vaccine.

While the present treatment method has been described primarily with respect to the use 0f attenuated virus vaccines of nonhuman origin, virus vaccines of human origin are also contemplated to be within the scope of the present invention. The present treatment method is intended to encompass any virus that is not pathogenic when administered to humans. Several types of attenuated viruses of human origin will be useful in the treatment method described herein. In particular, the following viruses of human origin, preferably in attenuated form, may be administered as described above with respect to the avian paramyxovirus: human myxovirus, human paramyxovirus, human poliovirus, human rotavirus, human vaccinia virus, human adenovirus and human herpesvirus. The aforementioned viruses may be employed in place of avian paramyxovirus or other viruses of nonhuman origin in the treatment of herpes, AIDS and viral neoplastic disease (cancer).

The efficacy of the present treatment method has been investigated for several different human diseases of viral and unknown etiology. Each specific disease investigated is discussed in a separate section below.

A. Herpes Virus Infections

In addition to causing the painful oral and genital lesions associated with Type 1 and Type 2 *Herpes simplex* and shingles (*Herpes zoster*), herpes viruses have been implicated as causative agents in certain types of cancers. Incompletely inactivated herpes viruses have been demonstrated to cause the malignant transformation of human cell cultures. Squamous cell carcinomas of the respiratory and gastrointestinal tracts, cervical carcinoma, Burkitt's lymphoma and nasopharyngeal carcinoma are examples of the types of cancers for which one of the various herpes viruses is possibly the etiological agent. Consequently, it is extremely important to terminate the chronic, recurrent infections characteristic of these viruses to avoid any casual relationship which may exist between the virus and these cancers. However, effective treatment which would eliminate these recurrent infections has not been available.

The treatment method of the present invention has proven to be effective in treating infections caused by herpes viruses and preventing recurrences. Avian paramyxovirus, in live attenuated form, was administered to several patients with histories of recurrent herpes simplex, genital herpes and herpes zoster infections. In most cases immediate improvement was experienced, with the drying of herpetic vesicles and relief of pain occurring rapidly. In many cases there was no recurrence following the administration of avian paramyxovirus vaccine.

The attenuated avian paramyxovirus vaccine was administered for five consecutive days at 4000 units per day. 1000 units was applied locally to the lesions in the form of the dry lyophilized powder, and 3000 units was administered intranasally in saline solution over about a 15 minute period. Clearing of the lesions and relief from pain usually could be observed within the five-day treatment period. It was discovered that unless administration of the attenuated virus was started within about two days after the first appearance of a herpetic lesion, the treatment was not as effective. About 80% of the patients treated for herpes did not require subsequent treatments. Those who did require further treatment experienced only mild recurrences of the disease.

Case History No. 1

This patient, who had suffered recurrent episodes of shingles (herpes zoster) for about 40 years, was treated with avian paramyxovirus as described above for five days at two to 3 month intervals for a two-year period. The shingles did not recur when the treatment was discontinued.

case History No. 2

This patient had suffered from recurrent shingles for over 25 years. The lesions cleared completely and pain disappeared after five days of treatment with avian paramyxovirus as described above. There was no recurrence for almost three years. At that time the patient experienced a stress-producing incident, which provoked a recurrence of the shingles. However, the patient's medical condition at the time precluded the administration of an attenuated virus.

Results similar to those described above were observed when genital herpes and oral herpes were treated with avian paramyxovirus.

Since the cytomegalovirus and Epstein-Barr virus are somewhat related to the herpes viruses, the present treatment method would also be expected to treat effectively the infectious diseases, such as infectious mononucleosis, caused by these viruses.

Avian rotavirus has also been shown to be a therapeutically effective treatment for *Herpes simplex* and *Herpes zoster* infections as well as for cytomegalovirus disease and infectious mononucleosis.

B. Hepatitis

Like the herpes virus, the hepatitis virus may cause chronic recurrent infections. However, hepatitis poses public health problems that are different from those which accompany herpes infections, therefore, and will be considered separately. There are actually several different viruses that cause hepatitis; of these hepatitis A virus (HAV) and hepatitis B virus (HBV) are the most common. Hepatitis A is transmitted by the fecaloral route by contaminated water, food and drink. Hepatitis B is transmitted by direct inoculation and close personal contact. There is currently no vaccine or special treatment available for hepatitis, and HAV infection is a major public health problem in many areas.

The present treatment method employing avian bursa virus (avian bursa virus) was studied in Marmoset monkeys, which are recognized to be a suitable experimental model for studying HAV. The virological, serological and pathological changes characteristic of HAV infections in human patients can be reproduced experimentally in monkeys. An experimental group of 20 Marmoset monkeys (*Saguinus labiatus labiatus*) was divided into 5 groups of 4 animals each and inoculated as follows:

Group 1: Saline
Group 2: HAV
Group 3: HAV and treated with avian bursa virus vaccine one week post-inoculation.
Group 4: HAV and treated with avian bursa virus vaccine 3 weeks post-inoculation.
Group 5: HAV and treated with avian bursa virus vaccine 5 weeks post-inoculation.

The bursa vaccine treatments were repeated for four consecutive days and consisted of 50 units orally and 50 units intranasally. The specific bursa virus vaccine used was Bursa-Vac No. G-603 from Sterwin Laboratories, Millsboro, Delaware.

Each animal was bled weekly, and percutaneous liver biopsies were performed biweekly, except for the fifth and sixth weeks. SGOT/SGPT levels were determined and tissue sections were histopathologically evaluated for evidence of hepatitis. All animals were sacrificed at 10 weeks, and necropsies were performed.

An exploratory experiment conducted prior to the main experiment demonstrated that the avian bursa virus did not affect the monkeys. The results of the main experiment were as follows:

Group 1: SGPT and biopsy normal; No evidence of hepatitis.
Group 2:
  Week 5—SGPT 6x normal; Histological evidence of hepatitis.
  Week 6—SGPT 2x normal; Histological evidence of hepatitis (inflammation less severe).
  Week 7—SGPT and liver biopsy normal.
Group 3: SGPT and biopsy normal; No evidence of hepatitis.
Group 4: Same as Group 3.
Group 5:
  Week 5—SGPT 5x normal; Histological evidence of hepatitis.
  Week 6—SGPT 2x normal; Histological evidence similar to Group 2.
  Week 7—SGPT and liver biopsy normal.

The autopsies were performed upon the sacrifice of the monkeys at 10 weeks. No gross pathology or liver pathology was observed in any of the animals. The levels of the SGOT enzymes were determined during the study, but did not change significantly. SGPT, rather than SGOT, however, is the more sensitive indicator of hepatitis in monkeys.

Group 5 was superinfected 5 weeks after HAV infection and did not show differences in SGPT and liver histopathology from the control group. The reason for this may be that, in Marmoset monkeys, the detectable symptoms are already present at 5 weeks. However, in humans the course of the disease is more severe and lasts longer; therefore the beneficial effects of the interfering virus could probably last much longer. Even when clinical signs are already present, the superinfecting virus is capable of interrupting the pathological process in any phase of the disease.

Patients with hepatitis treated according to the present method were also given avian rotavirus (bursa virus) vaccine. The treatment dosage was 2000 to 4000 units per treatment administered intranasally in saline. Many patients who have apparently recovered from hepatitis infections demonstrate increased bilirubin and enzyme levels, namely SGOT, SGPT and LDH, for over a year. Within two weeks after treatment with avian rotavirus, however, the bilirubin, SGOT, SGPT and LDH levels of hepatitis patients given this treatment returned to normal.

Case History No. 1

A 21 year old female with viral hepatitis and jaundice was treated with the avian rotavirus vaccine dosage described above. A significant reduction in total bilirubin and enzymes was achieved following only four treatments:

| Day | Total Bilirubin | SGPT | SGOT | LDH |
| --- | --- | --- | --- | --- |
| 1 | 5.7 | 1280 | 1750 | 240 |
| 3* | 10.6 | 2540 | 1700 | 235 |
| 5 | 11.7 | X | X | X |
| 6* | 9.8 | 1060 | 800 | 155 |
| 7* | 7.7 | 640 | 310 | 125 |
| 9* | 4.0 | 192 | 105 | 125 |
| 10 | 4.5 | 70 | 95 | 175 |
| 11 | 3.5 | 160 | 85 | 200 |
| 12 | 2.5 | 126 | 95 | 95 |
| 13 | 2.7 | X | X | X |
| 14 | 2.2 | 126 | X | 105 |
| 15 | 1.6 | 126 | 70 | 115 |
| 16 | 2.3 | 100 | 65 | 110 |
| 20 | 1.4 | 45 | 50 | 90 |

*Treatment administered
X Data not available

Case History No. 2

A 41 year old male who was alcoholic and suffering from extreme fatigue was diagnosed with acute hepatitis and treated with attenuated avian rotavirus. Within about two weeks of the initial treatment he felt normal and had a good appetite. Test results demonstrated the following improvement in bilirubin and blood enzyme levels:

| Day | Total Bilirubin | SGPT | Alkaline Phosphatase | LDH |
| --- | --- | --- | --- | --- |
| 1 | 2.0 | 2350 | 270 | 900 |
| 2* | X | X | X | X |
| 3* | 6.0 | 2080 | 281 | 487 |
| 5* | 7.5 | 950 | 263 | X |
| 6* | 8.2 | 476 | 259 | 269 |
| 7 | 9.4 | 253 | 251 | 228 |
| 8 | 10.3 | 235 | 267 | 289 |
| 9 | 8.3 | 182 | 259 | 251 |
| 12 | 3.4 | 141 | 197 | 190 |
| 16 | 2.2 | 85 | 140 | 220 |
| 23 | 2.1 | 79 | 110 | 222 |
| 33 | 1.7 | 143 | 75 | X |

*Treatment with avian rotavirus vaccine
X Data not available

Case History No. 3

A 38 year old female with fever, chills, fatigue, nausea, vomiting and dehydration was diagnosed with hepatitis and treated with avian rotavirus vaccine. After three treatments symptomatic and clinical improvements were noted.

| Day | Total Bilirubin | SGPT | Alkaline Phosphatase | LDH |
| --- | --- | --- | --- | --- |
| 1* | 2.5 | 246 | 185 | 254 |
| 4* | 3.0 | 155 | 220 | 280 |
| 7* | 0.7 | 82 | 222 | 191 |
| 10 | 1.0 | 197 | 160 | 65 |
| 11 | 0.7 | 42 | 154 | 203 |
| 14 | X | X | 133 | X |
| 18 | 0.7 | 37 | 103 | X |

*Treatment with avian rotavirus vaccine
X Data not available

Case History No. 3

A 23 year old male suffering from nausea, fatigue and abdominal discomfort was diagnosed with Hepatitis A and treated on five consecutive occasions with avian rotavirus vaccine. Improvements similar to those described above were also noted, and the patient's general condition improved in less than a week.

| Day | WBC | Total Bilirubin | SGPT | Alkaline Phosphatase | LDH |
| --- | --- | --- | --- | --- | --- |
| 1* | X | 3.0 | 292 | 211 | 438 |
| 2* | X | 3.4 | 420 | 210 | 419 |
| 3* | 14.8 | X | X | X | X |
| 4* | X | 4.2 | 410 | 283 | 420 |
| 5* | X | 4.1 | 510 | 277 | 361 |
| 7 | 12.1 | 2.0 | 60 | 320 | 750 |
| 8 | 10.1 | 0.8 | 67 | 240 | X |
| 9 | X | 1.2 | 63 | 177 | 298 |
| 13 | 8.3 | 1.1 | 29 | 120 | 213 |
| 31 | X | 0.2 | 16 | 60 | 194 |

*Treatment with avian rotavirus vaccine
X Data not available

The effect of avian bursa virus vaccine on acute Type B and on acute Type non-A non-B, or C, hepatitis was also evaluated. Patients of both sexes between the ages of 14 and 65 who were hospitalized and diagnosed with acute hepatitis, other than hepatitis A and toxic hepatitis, were included in the study, which lasted six months. The diagnosis of acute B or non-A, non-B hepatitis was established within one week of hospital admission and was based on clinical symptoms, laboratory tests, especially enzyme tests, and virus marker studies. Patients diagnosed with acute hepatitis A virus infection, toxic hepatitis, other virus hepatitis, or fulminant hepatitis were specifically excluded from the study. In addition, patients with systemic diseases such as diabetes or autoimmune disease or malignant tumors, or those who had received immunosuppressive treatment within 6 months were also excluded from the study.

The fifty-two patients participating in the study were examined and tested as follows:

1. Physical Examination immediately before treatment (0-time), then weekly after treatment, then monthly.
2. Virus Marker Studies immediately before treatment (0-time) and every six months. The following virus markers were evaluated at the stated intervals:
   a. HAV—at 0-time to exclude those who tested positive from the study.
   b. HBV (HBsAg; HBeAg, anti-HBsAg, delta) at 0-time, 3 months and 6 months.
3. Liver Function Tests (bilirubin, SGOT, SGPT. SAP, SGT, albumin)—at 0-time, then weekly, then monthly.

4. Other Laboratory Tests (RBC, WBC, ESR, urinalysis, creatinine)—at 0-time, every two weeks, then monthly.
5. Liver Biopsy—at 0-time for diagnostic purposes only and/or at the conclusion of treatment when chronic hepatitis was suspected.
6. Monitoring for possible side effects.

The avian bursa virus vaccine (BVV) in live attenuated form was administered to some of the patients by intranasal installation. The dose administered was 4000 units. This dose was given once daily during the first week, three times weekly during the second and third week and then once every month. Other patients were administered standard treatment, except cortico-steroid treatment. The vaccine was maintained at −20 C. until use and then was administered within 30 minutes of thawing.

The effectiveness of the bursa virus vaccine was determined by evaluating changes in laboratory parameters, such as blood enzyme levels, histological evidence, disappearance of the (B) virus antigen and changes in subjective parameters. A preliminary evaluation was made after two months of treatment and a final evaluation at the end of the study, after 6 months of treatment.

Of the fifty-two patients in the study, 25 were diagnosed with acute B hepatitis as verified by the presence of HBsAg, HBeAg and anti-HPcIgM antibody. Twenty-seven patients were diagnosed with acute C (non-A non-B) hepatitis by the exclusion of A, B virus, EBV, CMV infection and toxic hepatitis. As a result of the administration of bursa virus vaccine at the dosage levels and intervals described above, the first icteric phase was significantly shortened in both the B and C hepatitis groups. In the hepatitis B group two of the patients receiving the non-experimental treatment or placebos progressed into chronic hepatitis. None of the B-hepatitis patients receiving the bursa virus vaccine developed chronic hepatitis. No similar differences were observed in the hepatitis C group, however. Seroconversion, which in this study was the disappearance of HBsAg and the appearance of anti-HBe, was observed significantly earlier in the BVV-treated patients. In 3 patients the anti-C antibody titers fell below the detection threshold during the reconvalesence period. No significant side effects from the administration of the bursa virus vaccine to the hepatitis patients studied were observed.

The results of the study are set forth more specifically in Table 1 below:

TABLE 1

| Group | Remission | Remission within 1 mo. | Relapse |
|---|---|---|---|
| 1. Acute B | | | |
| BVV-Treated | 5.0 (2–10) | 5/12 | 1/12 |
| Placebo | 6.9 (2–12) | 8/13 | 7/13 |
| 2. Acute C | | | |
| BVV-treated | 6.2 (1–16) | 5/14 | 7/14 |
| Placebo | 8.1 (3–16) | 3/13 | 6/13 |

| Group | Active >6 mo. | CAH CPH | Sero-conversion |
|---|---|---|---|
| 1. Acute B | | | |
| BVV-Treated | 0/12 | 0/12 | 5/12 (8.8) |
| Placebo | 3/13 | 2/13 | 2/13 (16.8) |
| 2. Acute C | | | |
| BVV-Treated | 4/14 | 2/14 | 3/14 (12) |
| Placebo | 4/13 | 3/13 | 0/13 (0) |

Remission: mean and range (in weeks)
Remission with 1 mo: number of patients in remission within 1 month
Relapse: number of patients showing clinical and/or laboratory signs of relapse
Active >6 mo: elevated SGPT over 6 months, no histological signs of CPH
CAH/CPH: histologically verified
Seroconversion: number of patients (mean of weeks).
In hepatitis B group: disappearance of HBsAg, appearance of anti-HBe
In hepatitis C group: disappearance of anti-HC The foregoing study and results demonstrate that bursa virus vaccine appears to be a safe effective treatment for acute B and C viral hepatitis, and seems to produce more marked results in the treatment of B virus infections as compared to C virus infections.

C. Viral Neoplastic Diseases (Cancer)

The role of viruses in inducing cancers of various types has only recently begun to be demonstrated. Viruses have been implicated as etiological agents in several types of carcinoma. Once the tumor cells are present, their growth and survival and the formation of metastases depends, in part, on the anti-tumor responsiveness of the host organism. Theoretically, then, the amplification of the host's anti-tumor potential should cause the destruction of the tumor tissue. Preparations such as the interferons and Interleukin-2 that influence the biological response have been administered for this purpose with convincing results. Further, clinical observations have shown that an intercurrent virus infection may positively influence the course of some cancers to improve life expectancy. Besides probably enhancing the immune response of the host organism, treatment with an attenuated virus may modify the biodynamics of tumor cells and may ultimately lead to the destruction of the tumor cells. Consequently, the administration of attenuated viruses was investigated to substantiate these hypotheses. Although the exact mechanism by which the attenuated viruses achieve the results observed is not fully understood at this time, the administration of the avian and human viruses listed above in attenuated, inactivated or purified form to cancer patients appears to have therapeutic value and positively influences the course of the disease.

Animal studies have demonstrated the effect of a virus nonpathogenic to the animal on virus-caused tumors:

EXPERIMENT A

In this experiment, virus vaccines were tested against Rous sarcoma virus (RSV) in chickens. Four day old specific pathogen-free (SPF) chickens were used. Seven days prior to RSV infection, one group of 24 animals was inoculated with NDV vaccine intraorbitally; the second group of 24 animals with Marek's disease virus (MDV) vaccine intramuscularly; and the third group of 24 animals, with avian bursitis virus (ABuV) vaccine intramuscularly. Twelve animals in each group were separated and used as non-pathogenic virus controls. After 7 days, the three non-pathogenic virus-inoculated groups received RSV virulent virus injected into the right wing (in the humororadial region) in the amount cf 0.3 ml of a $10^{-3.7}$ dilution. At the same time, 15 chickens were inoculated only with RSV as controls. The number of dead animals was reported, and clinical observations were made during 5 weeks.

The results of this experiment are shown in Table I. Among the RSV controls, 72% of the animals died Among the preinoculated animals, the death rate was 58.8%, 40%, and 33.3% with MDV, NDV, and AbuV, respectively. Among the surviving animals, there were no tumors in those animals which were preinoculated with ABuV. However, in all other groups, including the RSV control group, tumors still were seen beyond 5 weeks. In this experiment, a significant reduction was demonstrated on an ongoing virus effect (RSV) using a non-pathogenic vaccine strain (ABuV). This vaccine not only reduced the mortality rate by more than 50% but almost completely eliminated the clinical manifestations in surviving animals.

TABLE 2

Interference Between Rous Sarcoma Virus (R.S.) and Three Selected Animal Live Vaccines 4-Day Old Specific Pathogen-Free Chickens

| No. of Animals Vaccinated | No. of Animals Post-Inoculated 7 Days Later | No. of Single Virus Control Animals | No. of Animals Dead After 5 Wks. of Rous Sarcoma Inoculation: Virus Control | No. of Animals Dead After 5 Wks. of Rous Sarcoma Inoculation: Combined Inoculation | Neoplasma in Surviving Animals At the Site of RS Virus Inoculation |
|---|---|---|---|---|---|
| 24 Marek Disease Vaccine I.m. | 12 R.S. I.m. | 12 Marek Disease Vaccine | 0.0% | 58.3% | Still Present |
| 30 Newcastle Disease Vaccine I.o.** | 15 R.S. I.m. | 15 Newcastle Disease Vaccine | 0.0% | 40.0% | Still Present in Reduced No. of Animals |
| 24 Avian Bursa Disease Vaccine I.m. | 12 R.S. I.m. | 12 Avian Bursa Disease Vaccine | 0.0% | 33.3% | Regressed |
| — | 15 R.S. I.m. | 15 Rous Sarcoma Virus | 72.0% | — | Still Present |
| 15 Uninoculated Controls | — | — | — | — | Not Present |

*I.m. intramuscularly
**I.o. intraorbitally lation with the IBR, ABV and AEV vaccines did not increase the survival rate over that of the control group, although the mortality of Group 5 (ABV) was slightly less than the others.

The study also investigated whether a known potentiating agent, such as chlorpromazine hydrochloride, would have potentiating effect on the activity of NDV-H in the MAV system previously studied. The NDV-H vaccine prepared as described above was mixed with chlorpromazine hydrochloride (1.25 mg/0.5 ml). This mixture was added to 0.5 ml undiluted MAV collected from the ascites fluid obtained from infected mice and injected intraperitoneally into susceptible Swiss mice. By the end of the observation period none of the mice had died, and the development of ascites fluid was delayed beyond what had previously been observed.

Viruses of nonhuman origin were administered in attenuated form to patients, some terminally ill, diagnosed with various cancers that had not responded to other available treatment methods, such as chemotherapy or radiation. Although the previous administration of chemotherapy appeared to have a negative effect on the course of the disease in patients subsequently treated with attenuated virus vaccines, most patients responded extremely well to the present treatment method.

EXPERIMENT B

In an additional study, 96 young adult Swiss mice, 12 in each group, were infected with the pathogenic mouse ascites-associated lymphoma virus (MAV) and concurrently inoculated with 0.5 ml of an undiluted suspension of one of seven different virus vaccines The vaccines were prepared in isotonic saline diluent from freeze-dried live vaccines. The MAV was collected in undiluted ascites fluid from the abdomens of infected mice. Inoculations were performed intraperitoneally. The animals were observed for one month, and the mortality rates were evaluated In addition, development of ascites was noted since this is an indication of lymphoma activity.

Each group was inoculated as follows:

Group 1: MAV and rabies vaccine (RV)
Group 2: MAV and Newcastle disease vaccine, Strain H (NDV-H)
Group 3: MAV and avian encephalmyelitis vaccine (AEV)
Group 4 MAV and infectious bovine rhinotracheitis vaccine (IBR)
Group 5: MAV and avian bronchitis vaccine (ABV)
Group 6: MAV and parvovirus vaccine (PV)
Group 7: MAV and reovirus vaccine (REV)
Group 8: MAV control The results of this study are shown graphically in FIG. 1. Group 2, which had been inoculated with both MAV and Newcastle disease virus vaccine, was the only group in which none of the mice died within 30 days. In addition, only 3 of the mice developed ascites The RV-inoculated mice did not develop ascites The cause of death in those cases was determined to be rabies Inocu-

Case History No. 1

A 45 year old female was diagnosed with infiltrating duct carcinoma of the breast with metastasis to more than four axillary nodes. A modified mastectomy was performed, and no chemotherapy was administered at the patient's request. Beginning immediately after surgery and continuing for two years, this patient was treated with attenuated virus vaccine. 4000 units was administered daily for 30 days and then twice weekly for four months. This treatment was then repeated for the two-year period. The patient has remained free of symptoms and has shown no evidence of the cancer.

Case History No. 2

A 75 year old male was diagnosed with colorectal carcinoma with metastases to the liver and pleura. An abdominoperineal resection was performed. A minimal dose of chemotherapy was administered and discontinued because of negative side effects. 50,000 units of attenuated avian paramyxovirus vaccine was instilled into the colostomy weekly for three months. Although the patient died seven months after surgery, the cause of death was cardiac-related, and a complete autopsy showed no residual cancer in any organ.

Case History No. 3

A 73 year old female with colorectal carcinoma which had metastasized to regional lymph nodes underwent an abdominoperineal resection and, five months later, the surgical removal of a nut-sized metastatic lymph node. A CAT scan eight months after surgery demonstrated numerous tumor masses in the pelvic area as well as probable sacral bone destruction. 1,000,000 units of attenuated avian paramyxovirus vaccine was administered on three successive days and then 2,000 units was administered every second day for nine months. Within three months after the initial treatment, a CAT scan showed no definite signs of metastasis. A CAT scan one year after the initial treatment was negative, and the patient was symptom free.

Case History No. 4

A 61 year old male with colorectal adenocarcinoma which had metastasized to the lymph nodes was operated on and the sigmoid colon was surgically resected. Four months after surgery the tumor showed signs of progression. 4000 units of attenuated avian paramyxovirus was administered daily for two weeks, and then 1000 units was given daily for 40 days. The patient is currently free of symptoms.

The dosage of attenuated virus vaccine administered to cancer patients has varied depending upon the type of cancer and the response shown by the patient to the vaccine. Typically 4000 units of the vaccine have been administered daily for one month and then 4000 units at least three times per week for three to six months to achieve beneficial results in cancer patients. 2000 of these units is administered rectally, and the remaining 2000 is administered intranasally. However, other dosage levels and treatment periods may be effective as well and are also contemplated to be within the scope of the present invention.

D. Aphthous Stomatitis.

Aphthous stomatitis bears many similarities to oral herpes; however, the etiology of this disease is unknown. The infection is characterized by single or multiple acute painful ulcers on the oral mucosa that chronically recur. The lesions usually heal spontaneously in about 7 to 10 days. Recurrences may be as seldom as 2 to 3 times a year or as frequently as once a month. In some cases the lesions may be present almost constantly. The number of ulcers that recur may vary from one to a very large number. At the present time antiviral agents such as Zovirax may provide some relief; however, these agents have not been effective in preventing recurrence of the stomatitis.

Case History No. 1

A male, age 30, was treated for recurrent and almost constant mouth ulcers, diagnosed as aphthous stomatitis, which varied in number from 1 to 5 at a time. Zovirax in the form of capsules, one to be taken 5 times each day as needed, were prescribed. After about 4 months, the stomatitis returned. At this time weekly injections of Newcastle Disease virus vaccine were administered. 1000 units of the vaccine was given intramuscularly for eight weeks. At the end of eight weeks the aphthous stomatitis had cleared completely and has not recurred.

Case History No. 2

Six family members were diagnosed with aphthous stomatitis. Five of the six were given 2000 units of attenuated avian paramyxovirus vaccine locally and orally on four occasions over a two-week period. The lesions cleared and have not recurred. However, the sixth untreated family member has experienced repeated recurrences.

E. Acquired Immune Deficiency Syndrome (AIDS)

Acquired Immune Deficiency Syndrome (AIDS) is an acute disease caused by a virus identified in 1984 and designated as human T-lymphadenopathy-associated type III/lymphadenopathy-associated virus (HTLV-III/LAV), which is a single stranded RNA (ribonucleic acid) retrovirus. HTLV-III/LAV binds to a receptor present on the surface of T-4 lymphocytes, the white blood cells responsible for controlling immune response. The mechanism of HTLV-III/LAV virus' initial invasion of T-4 lymphocytes appears to be very similar to that of any other single strand RNA virus. Once the virus has invaded a T-4 cell and taken over its genetic machinery, there is usually a long dormant period that may last many years. Once activated, however, the AIDS virus is capable of extremely rapid replication, which is thought to be caused by the transacting transcriptional regulation (TAT) property possessed by this virus. The result of this rapid replication of HTLV-III/LAV viruses has a devastating destructive effect on the entire immune system characterized by a progressive depletion of T-4 helper-inducer T cells and a decreased ratio T-4 of helper-inducer to cytotoxic T-8 lymphocytes.

This knowledge has facilitated the development of useful screening tests for drugs active against HTLV-III/LAV virus that may have a therapeutic effect in persons already infected with the AIDS virus. However, to date, even with the availability of such tests and notwithstanding that compounds and compositions too numerous to catalogue here have been tried in an effort to reduce or stop the explosive spread and increased prevalence of this deadly viral infection, no cure has been found and no vaccine has been identified. Even symptomatic relief has come from just one drug, azidothymidine (AZT). While it is not a cure and does not destroy the virus, AZT stops the virus from replicating. Notwithstanding that AZT may induce serious side effects and has primarily been tested only on patients who have *Pneumocystic carinii* pneumonia (PCP), it is the only drug approved for distribution to AIDS victims.

AIDS and AIDS related complex (ARC) have become a major public health problem of epidemic proportions over the last few years. Various antiviral agents directed at inhibiting the infectivity and replication of the virus have been proposed and are currently being tested. To date none has achieved the desired result of inhibiting the action of the virus while allowing the immune system to be restored to a level of immunocapability that will allow it to develop resistance to the AIDS virus and to the debilitating opportunistic infections that accompany AIDS.

A limited study has been conducted to ascertain whether the apathogenic viruses discussed above have any effect on the course of AIDS and ARC. Avian paramyxovirus vaccine, specifically Newcastle disease virus, Strain H, was administered to AIDS and ARC patients. The vaccine was administered in attenuated form at 1000 units weekly by intramuscular injection. Improvement was noted in delayed type hypersensitivity, and the degree of lymphadenopathy and hepatosplenomegaly decreased. Marked symptomatic improvement was observed, particularly in the degree of fevers, night sweats, chills and fatigue There was no weight loss by the patients in the study. In addition, oropharyngeal candidiasis improved rapidly.

The results of the laboratory tests conducted on these patients demonstrated improvement in liver function tests, with elevated SGOT, SGPT, Gamma-GT and alkaline phosphatase levels returning to normal limits within two weeks. Elevated serum triglyceride levels characteristic of AIDS-related hepatocellular disorder returned to less than 200 mg/dl in many cases. Sedimentation rates were demonstrated to decrease. In addition, antibody titers to viruses commonly coexistent with the AIDS virus, particularly those of the Herpes group such as Cytomegalovirus, Hepatitis-B, and Epstein-Barr, were shown to decrease substantially. In the cases in which the vaccine was administered over a period of time, depressed circulating leukocyte and platelet counts increased. Moreover, a gradual increase in absolute T-4 counts was observed.

It was noted during this limited study that the concurrent administration of the Newcastle disease virus vaccine and AZT appeared to increase the antiviral activity of both agents.

The following case histories present these observations in more detail:

Case History No. 1

A 35 year old male with AIDS was also determined to have PCP, Kaposi's sarcoma, and Candidiasis. The patient had lost 14 pounds over the previous 9 weeks, showed liver enlargement, and his lungs were not clear. Medications at that time included Interferon, AZT, Zovirax, Triple Sulfa, Pentamidine Isothionate IV by inhalation, Lodamil, Tigon, Advil and a cough medication. Mycostatin was added to treat the Candidiasis. 1000 units of Newcastle disease virus vaccine was given by intramuscular injection and intramuscular injections of 1000 units were continued at weekly intervals. Interferon was discontinued, but AZT was not. In addition, the Pentamidine therapy was continued. Within 4 weeks following the initial treatment, the lungs were clear with no rhonchi or cough. Within 8 weeks the Kaposi's sarcoma lesions were significantly lighter, and the patient's general condition had improved significantly. Substantial increases in the platelet and white blood cell counts were noted as follows:

| | Initial | 4 Weeks | 8 Weeks |
|---|---|---|---|
| Platelets (thou/mm) | 157 | 230 | 292 |
| WBC (thou/mm) | 1.5 | 2.4 | 3.10 |

The normal reference range for platelets is 140–440 thou/mm and for white blood cells is 4.8–10.8 thou/mm The initial T4 was 73/cubic mm, and after 4 weeks the T-4 had increased to 218/cubic mm. The normal reference range for T4 cells is 537–1,571/cubic mm.

Case History No. 2

A 33 year old male with AIDS was seen after about 5 months of AZT therapy complaining of fatigue and tightness in the chest determined to be caused by PCP. After about 10 days of Pentamidine Isophionate IV, the PCP appeared to be resolved. Within another month, the patient had gained 7 pounds, and his lungs were clear. This patient was seen again 3 months later with shortness of breath and other symptoms of PCP as well as thrush on his tongue. Pentamidine was administered by inhalation therapy. In addition, 1000 units of the Newcastle disease virus vaccine was given by intramuscular injection and this dose continued weekly. After 4 weeks the T4 count has increased from 14/cubic mm to 38/cubic mm. Although the T4 count was still substantially below normal, the patient's clinical signs showed improvement and his lungs were clear.

Case History No. 3

A 37 year old male diagnosed with AIDS and a history of herpes was examined and found to have an enlarged liver and spleen, thrush, an apparently fungal perianal inflammation, and audible rhonchi and wheezing in the lungs. This patient additionally had repeated staphylococcal and candidal infections and was following a course of AZT therapy. The T4 count at the time of examination was 30/cubic mm. 1000 units of MTH-68 was given by intramuscular injection, and AZT thereby was continued. One week later the T4 count had increased to 540/cubic mm, and much improvement of the clinical symptoms was noted.

Case History No. 4

A 43 year old male with AIDS was given weekly intramuscular injections of 1000 units of Newcastle disease virus vaccine. When this patient was first seen, his T4 count was 178/cubic mm, the platelet count was 29.0 thou/cubic mm, and the white cell count was 14.1 thou/cubic mm. Normal ranges for these blood components are 537–1,571/cubic mm, 140–440 thou/cubic mm. and 3.90–11.3 thou/cubic mm, respectively. 1000 units of Newcastle disease virus vaccine was given by intramuscular injection once weekly. The T4 count increased to 479, the platelet count increased to 69.0 thou/cubic mm, and the white cell count decreased to 9.40 thou/cubic mm, within normal limits, over a 4 week period.

Case History No. 5

This patient was a 27 year old male diagnosed with AIDS. His initial T4 count was 70/cubic mm. After 4 weeks of weekly intramuscular injections of 1000 units of Newcastle disease virus vaccine, the T4 count increased to 269/cubic mm. The white cell and platelet counts were also within normal limits.

F. Polyarteritis Nodosa

Whether this disease is of viral etiology is not known. It was at one time assumed to be an allergic reaction to some as yet unknown agent because of the similarities in the arterial lesions of patients with polyarteritis nodosa and those developing hyperimmune reactions, such as to drugs or foreign proteins. The distinguishing feature of the disease is focal swelling of collagen fibers limited to the media and adventitia of the smaller arteries. White blood cells and plasma cells accumulate at these foci. The vessel lumen narrows, the vessel wall weakens, and aneurysms may form and rupture. The lesion usually heals in a few weeks or months, and fibroblasts replace the original arterial tissue. Diagnosis is often difficult since acute polyarteritis nodosa may resemble many other primary infectious diseases. The outlook is not favorable once the disease has been diagnosed. Corticosteriods may provide good symptomatic response; however, this may often be only temporary.

It has been discovered, however, that the administration of live attenuated Newcastle disease virus vaccine can be of value in treating polyarteritis nodosa. A 57 year old male was diagnosed as having acute polyarteritis nodosa. The administration of 50 mg/day of prednisone resulted in improvement of symptoms, but within 6 months he suffered a relapse despite an increase in prednisone to 80 mg/day and became moribund. The administration of large doses of attenuated Newcastle disease virus vaccine resulted in rapid and dramatic improvement, with a muscle biopsy showing healing vasculitis. A second relapse occurred 3 months later, and inoculations of Newcastle disease virus and avian bronchitis virus vaccines were administered. The prior rapid, dramatic improvement was repeated. The patient's muscle strength increased, he regained his ability to walk, he gained weight, and other symptoms subsided. A muscle biopsy and other studies performed 5 months later showed significant improvement. Within another 8 months electromyography and nerve conduction were normal, and within an additional 5 months the patient was asymptomatic and laboratory tests revealed results within normal ranges.

Attenuated virus vaccines have been administered to a small number of patients with other diseases of unknown etiology, namely, rheumatoid arthritis and multiple sclerosis, with similar dramatic improvement in clinical condition as in the viral diseases described above. One patient with arthritis who experienced great difficulty walking was given 2000 to 4000 units of avian paramyxovirus in attenuated form twice a week for three months and was then able to dance. The patient has not noted any recurrence of symptoms. Another arthritis patient originally unable to bend her joints was given 4000 units of attenuated virus vaccine every two days for two weeks and then once each week for about five months. Improvement in her clinical condition was noted within two weeks. In additional two patients with multiple sclerosis treated with attenuated virus vaccines showed similar improvement.

Although the present treatment method has been described with respect to the administration of one type of attenuated virus, mixtures of different viruses could also be administered. In addition, one type of attenuated virus could be administered initially, followed by treatment with a different type of attenuated virus. Additionally, mixtures of viruses of human origin and viruses of nonhuman origin may be administered in attenuated form in accordance with the present treatment method.

Industrial Applicability

The treatment method of the present invention will find its primary application in the treatment of diseases of known viral etiology. However, based upon the remarkable results achieved in the treatment of polyarteritis nodosa, the use of attenuated apathogenic viruses may ultimately be shown to have a much broader application. Although only a small number of viruses apathogenic to humans has been investigated thus far, it is likely that many more will be found to be efficacious in the treatment of human diseases of viral etiology.

We claim:

1. A method of significantly increasing the numbers of T-4 helper-inducer T cells, white blood cells and platelets in humans infected with acquired immune deficiency syndrome and acquired immune deficiency syndrome-related complex and displaying clinical indications of said infection by administering to said infected humans 1000 units of an attenuated avian paramyxovirus by intramuscular injection one time each week for at least four weeks.

2. A method of treating humans infected with hepatitis B virus or hepatitis C virus and displaying clinical indications of said infection by administering to said infected humans a therapeutically effective amount of an attenuated avian bursa virus vaccine.

3. The method described in claim 2, wherein said therapeutically effective amount comprises 4000 units of bursa virus vaccine administered intranasally at intervals ranging from daily to monthly for a period of at least about two months.

4. A method for reducing the duration of the acute phase of hepatitis infection and significantly enhancing seroconversion in human patients infected with hepatitis B virus, hepatitis C virus or both hepatitis B virus and hepatitis C virus by administering to said infected patients an amount of attenuated avian bursa virus vaccine effective to decrease the length of said acute phase and to enhance seroconversion.

5. The method described in claim 4, wherein said amount comprises 4000 units of said bursa virus vaccine administered daily for one week, three times per week for two weeks and monthly for six months.

6. A method of treating human patients infected with hepatitis virus and characterized by positive virus markers for hepatitis virus, abnormal liver function, and abnormal physical and clinical symptoms which causes the production of antibodies to said hepatitis virus and causes said abnormal liver function and said abnormal physical and clinical symptoms to return to normal, said method comprising the administration to an infected patient of an amount of attenuated avian bursa virus vaccine effective to produce said antibodies and to return said liver function and said physical and clinical symptoms to normal.

7. The method described in claim 16, wherein said virus markers include HAV, HBV and B (non-A non-B)V.

8. The method described in claim 7, wherein the amount of said attenuated avian bursa virus vaccine administered to said patients at each treatment is 4000 units of said attenuated avian bursa virus vaccine.

9. The method described in claim 8, wherein said 4000 units of attenuated avian bursa virus vaccine is administered to said patients intranasally in a saline solution.

* * * * *